United States Patent
Lee et al.

(10) Patent No.: US 9,649,533 B2
(45) Date of Patent: May 16, 2017

(54) HUMAN MUSCULAR STRENGTH AMPLIFICATION ROBOT DRIVEN BY INTENTION OF USER AND DRIVING METHOD THEREOF

(71) Applicant: Korea Polytechnic University Industry Academic Cooperation Foundation, Siheung-si (KR)

(72) Inventors: Eung-Hyuk Lee, Bucheon-si (KR); Jee-Hwan Ryu, Cheonan-si (KR); Su-Hong Eom, Incheon (KR); Seoung-Jun Lee, Cheonan-si (KR)

(73) Assignee: Korea Polytechnic University Industry Academic Corporation Foundation, Siheung-si (KR)

( * ) Notice: Subject to any disclaimer, the term of this patent is extended or adjusted under 35 U.S.C. 154(b) by 0 days.

(21) Appl. No.: 14/952,101

(22) Filed: Nov. 25, 2015

(65) Prior Publication Data
US 2016/0158601 A1      Jun. 9, 2016

(30) Foreign Application Priority Data
Dec. 4, 2014 (KR) .................. 10-2014-0172593

(51) Int. Cl.
*A63B 24/00* (2006.01)
*B25J 9/00* (2006.01)
*B25J 13/08* (2006.01)

(52) U.S. Cl.
CPC ......... *A63B 24/0062* (2013.01); *B25J 9/0006* (2013.01); *B25J 13/085* (2013.01)

(58) Field of Classification Search
CPC .... A63B 24/00; A63B 24/0062; B25J 9/0006; B25J 13/085
See application file for complete search history.

(56) References Cited

U.S. PATENT DOCUMENTS

| | | | | |
|---|---|---|---|---|
| 4,235,437 A | * | 11/1980 | Ruis ................ | A63B 21/00178 482/113 |
| 2009/0215588 A1 | * | 8/2009 | Riener ................ | A61H 1/0237 482/7 |
| 2015/0122018 A1 | * | 5/2015 | Yuen ..................... | G01B 21/16 73/384 |
| 2015/0265358 A1 | * | 9/2015 | Bowling ................ | A61B 34/32 700/261 |
| 2016/0101517 A1 | * | 4/2016 | Kornbluh ............... | B25J 9/0006 482/78 |

* cited by examiner

*Primary Examiner* — Glenn Richman
(74) *Attorney, Agent, or Firm* — Workman Nydegger

(57) ABSTRACT

A muscular strength enhancing robot to be driven by an intention of a user and a method of driving the robot are disclosed. The robot includes an actuator attached to a portion of a body of the user and configured to be actuated by enhancing a muscular strength, an encoder connected to the actuator and configured to measure an actual velocity at which the actuator moves, a force or torque sensor configured to measure an intensity of a force to be applied, an admittance modeling module configured to calculate a target velocity using the intensity of the force, and a proportional integral derivative (PID) control module configured to control actuation of the actuator in proportion to a velocity difference between the target velocity and the actual velocity, control the actuation by a cumulative value of the velocity difference, and control the actuation by a difference between a previous and a current velocity difference.

10 Claims, 3 Drawing Sheets

HUMAN MUSCULAR STRENGTH AMPLIFICATION ROBOT DRIVEN BY INTENTION OF USER AND DRIVING METHOD THEREOF

CROSS-REFERENCE TO RELATED APPLICATION

This application claims the priority benefit of Korean Patent Application No. 10-2014-0172593, filed on Dec. 4, 2014, in the Korean Intellectual Property Office, the disclosure of which is incorporated herein by reference.

BACKGROUND

1. Field of the Invention

Embodiments relate to a muscular strength enhancing robot and a method of driving the robot, and more particularly, to a muscular strength enhancing robot driven by an intention of a user and a method of driving the robot.

2. Description of the Related Art

A muscular strength enhancing robot operates for rehabilitation or assistance in surmounting disabilities while being worn on a portion of a body of a user. Such a robot may detect a small movement of the portion and increase a velocity and strength of the movement.

The detecting of the movement may be performed based on a change in acceleration, and a speed and a direction at and in which the robot is driven may be determined based on the acceleration.

When the user permanently wears the robot, a weight of the robot may add a considerable load to the user. Thus, efforts have focused on providing a lighter and more wearable robot while maintaining a function of the robot.

However, such efforts may generate side effects in terms of a system function.

For example, in a case of a muscular strength enhancing robot with a small mass, acceleration may change greatly by a slight change in strength, and thus an operation speed to be calculated therefrom may be unintentionally incorrect.

In detail, a total input energy of a system of the robot, which is associated with the acceleration, may become smaller than a total output energy of the system. In such a case, the system may become unstable, and thus malfunction and functional deterioration may occur.

In such a case when the total output energy of the system is greater than the total input energy of the system, the system may be in an active state, which indicates that the system is unstable. Conversely, when the total output energy is less than the total input energy, the system may be in a passive state, which indicates that the system operates stably.

Thus, there is a desire for technology for minimizing a side effect occurring from weight lightening of a muscular strength enhancing robot and for stabilizing a system of the robot.

SUMMARY

An aspect provides a muscular strength enhancing robot to be driven based on an intention of a user.

Another aspect also provides a method of driving a muscular strength enhancing robot based on an intention of a user.

According to an aspect, there is provided a muscular strength enhancing robot to be driven based on an intention of a user, the robot including an actuator attached to a portion of a body of the user and configured to be actuated by enhancing a muscular strength in a movement direction in which the portion moves, an encoder connected to the actuator and configured to measure an actual velocity $v_r$ at which the actuator moves in the movement direction, a force or torque sensor configured to measure an intensity of a force $f_h$ to be applied in the movement direction, an admittance modeling module configured to calculate a target velocity $v_d$ using the intensity of the force $f_h$ measured by the force or torque sensor, and a proportional integral derivative (PID) control module configured to control actuation of the actuator in proportion to a velocity difference $v_e$ between the target velocity $v_d$ calculated by the admittance modeling module and the actual velocity $v_r$ measured by the encoder, control the actuation of the actuator by a cumulative value of the velocity difference $v_e$, and control the actuation of the actuator by a difference between a previous velocity difference $v_e$ and a current velocity difference $v_e$.

The robot may further include an input energy calculating module configured to calculate a current input energy $E_{in}(k)$ of the robot, an output energy calculating module configured to calculate a current output energy $E_{out}(k)$ of the robot, and a passivity control module configured to determine stability of a system of the robot by comparing the calculated current input energy $E_{in}(k)$ to the calculated current output energy $E_{out}(k)$, and calculate a damping element $\beta$ and apply the calculated damping element $\beta$ to the actuator in response to a determination that the system is unstable.

The input energy calculating module may calculate the current input energy $E_{in}(k)$ by calculating an instantaneous input energy using the force $f_h$ measured by the force or torque sensor and the target velocity $v_d$ calculated by the admittance modeling module, and adding the calculated instantaneous input energy and a previous input energy.

The output energy calculating module may calculate the current output energy $E_{out}(k)$ by calculating an instantaneous output energy using a force $f_c$ of controlling the actuation of the actuator by the PID control module and the target velocity $v_d$ calculated by the admittance modeling module, and adding the calculated instantaneous output energy and a previous output energy.

The passivity control module may calculate the damping element based $\beta$ on the following Equation, $$\beta(k) = \begin{cases} -\dfrac{E_{obs}(k)}{(f_c)^2 \Delta T}, & \text{if } E_{obs} < 0 \text{ and } f_c \neq 0 \\ 0, & \text{if } E_{obs} \geq 0 \text{ or } f_c = 0 \end{cases} \quad \text{[Equation]}$$

wherein "$E_{obs}(k)$" is a value obtained by subtracting a value of $E_{out}(k)$ from a value of $E_{in}(k)$ ($E_{in}(k)-E_{out}(k)$) and "$\Delta T$" denotes a sampling time.

According to another aspect, there is provided a method of driving a muscular strength enhancing robot based on an intention of a user, the method including measuring, by an encoder connected to an actuator, an actual velocity $v_r$ at which the actuator moves in a movement direction in which a portion of a body of the user to which the actuator is attached moves, measuring, by a force or torque sensor, an intensity of a force $f_h$ to be applied in the movement direction, calculating, by an admittance modeling module, a target velocity $v_d$ using the intensity of the force $f_h$ measured by the force or torque sensor, and controlling actuation of the actuator in proportion to a velocity difference $v_e$ between the target velocity $v_d$ calculated by the admittance modeling module and the actual velocity $v_r$ measured by the encoder, controlling the actuation of the actuator by a cumulative value of the velocity difference $v_e$, and controlling the actuation of the actuator by a difference between a previous velocity difference $v_e$ and a current velocity difference $v_e$, by a PID control module.

The method may further include calculating, by an input energy calculating module, a current input energy $E_{in}(k)$ of the robot, calculating, by an output energy calculating module, a current output energy $E_{out}(k)$ of the robot, and determining, by a passivity control module, stability of a system of the robot by comparing the calculated current input energy $E_{in}(k)$ to the calculated current output energy $E_{out}(k)$, and calculating a damping element β and applying the calculated damping element β to the actuator in response to a determination that the system is unstable, by the passivity control module.

The calculating of the current input energy $E_{in}(k)$ may include calculating the current input energy $E_{in}(k)$ by calculating an instantaneous input energy using the force $f_h$ measured by the force or torque sensor and the target velocity $v_d$ calculated by the admittance modeling module, and adding the calculated instantaneous input energy and a previous input energy.

The calculating of the current output energy $E_{out}(k)$ may include calculating the current output energy $E_{out}(k)$ by calculating an instantaneous output energy using a force $f_c$ of controlling the actuation of the actuator by the PID control module and the target velocity $v_d$ calculated by the admittance modeling module, and adding the calculated instantaneous output energy and a previous output energy.

In response to the determination that the system is unstable, the calculating of the damping element β and the applying of the calculated damping element β to the actuator by the passivity control module may include calculating the damping element β based on the following Equation, $$\beta(k) = \begin{cases} -\dfrac{E_{obs}(k)}{(f_c)^2 \Delta T}, & \text{if } E_{obs} < 0 \text{ and } f_c \neq 0 \\ 0, & \text{if } E_{obs} \geq 0 \text{ or } f_c = 0 \end{cases} \quad \text{[Equation]}$$

wherein "$E_{obs}(k)$" is a value obtained by subtracting a value of $E_{out}(k)$ from a value of $E_{in}(k)$ ($E_{in}(k)-E_{out}(k)$) and "$\Delta T$" denotes a sampling time.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Figure 1:
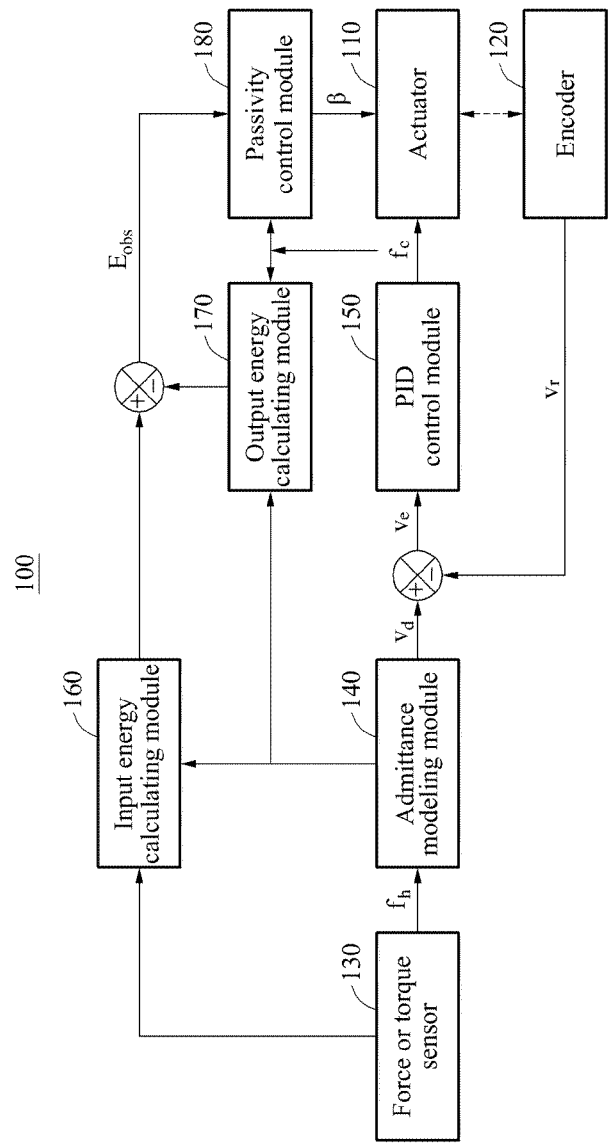
FIG. 1 is a diagram illustrating a configuration of a muscular strength enhancing robot to be driven based on an intention of a user according to an embodiment.

Hereinafter, reference will now be made in detail to examples with reference to the accompanying drawings, wherein like reference numerals refer to like elements throughout.

Various alterations and modifications may be made to the examples. Here, the examples are not construed as limited to the disclosure and should be understood to include all changes, equivalents, and replacements within the idea and the technical scope of the disclosure.

Terms such as first, second, A, B, (a), (b), and the like may be used herein to describe components. Each of these terminologies is not used to define an essence, order or sequence of a corresponding component but used merely to distinguish the corresponding component from other component(s). For example, a first component may be referred to as a second component and, similarly, a second component may be referred to as a first component. In addition, the term "and/or" includes any and all combinations of one or more of the associated listed items.

It should be noted that if it is described in the disclosure that one component is "connected," "coupled," or "joined" to another component, a third component may be "connected," "coupled," and "joined" between the first and second components, although the first component may be directly connected, coupled, or joined to the second component.

It should also be noted that if it is described in the disclosure that one component is "directly connected," "directly coupled," or "directly joined" to another component, a third component may not be present between the two components.

The terminology used herein is for the purpose of describing particular embodiments only and is not intended to be limiting. As used herein, the singular forms "a," "an," and "the," are intended to include the plural forms as well, unless the context clearly indicates otherwise.

It should be further noted that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof Unless otherwise defined, all terms including technical and scientific terms used herein have the same meaning as commonly understood by one of ordinary skill in the art to which this disclosure belongs.

Thus, it should be further noted that terms, such as those defined in commonly used dictionaries, are interpreted as having a meaning that is consistent with their meaning in the context of the relevant art and are not interpreted in an idealized or overly formal sense unless expressly so defined herein.

Hereinafter, example embodiments will be described in detail with reference to the accompanying drawings.

FIG. 1 is a diagram illustrating a configuration of a muscular strength enhancing robot to be driven based on an intention of a user according to an embodiment. The muscular strength enhancing robot to be driven by an intention of a user will be simply referred to as a muscular strength enhancing robot 100.

Referring to FIG. 1, the muscular strength enhancing robot 100 includes an actuator 110, an encoder 120, a force or torque sensor 130, an admittance modeling module 140, a proportional integral derivative (PID) control module 150, an input energy calculating module 160, an output energy calculating module 170, and a passivity control module 180.

The muscular strength enhancing robot 100 is configured to compare, in real time, an input energy in a system of the muscular strength enhancing robot 100 to an output energy in the system, and control an operation speed of the actuator 110 by applying a damping element in response to a current output energy of the system being greater than a current input energy of the system and the system thereby being active.

The muscular strength enhancing robot 100 to which a realtime feedback actuation control is applied is configured to reduce the operation speed of the actuator 110, prevent a cumulatively excessive input energy from being input, and gradually stabilize the entire system.

Hereinafter, each component of the muscular strength enhancing robot 100 will be described in detail.

The actuator 110 may be attached to a portion of a body of a user, for example, an arm and a leg of the user.

The actuator 110 is configured to be actuated by enhancing a muscular strength in a movement direction in which the portion of the body to which the actuator 110 is attached moves.

The encoder 120 is connected or attached to the actuator 110, and configured to measure an actual velocity vr at which the actuator 110 moves in the movement direction.

The encoder 120 is configured to measure an actual rotation angle of a motor of the actuator 110.

The force or torque sensor 130 is configured to measure an intensity of a force fh to be applied in the movement direction of the portion of the body. The force or torque sensor 130 is configured to measure the intensity of the force fh by detecting a minute movement of the portion of the body.

The admittance modeling module 140 is configured to calculate a target velocity vd using the intensity of the force fh measured by the force or torque sensor 130.

The admittance modeling module 140 is configured to calculate the target velocity vd by calculating an acceleration ad using the force fh measured by the force or torque sensor 130 and a mass of the muscular strength enhancing robot 100 based on the Newton's Second Law, and performing integration on the calculated acceleration ad.

The PID control module 150 is a control module configured to control actuation (or operation) of the actuator 110, and uses proportional control, integral control, and derivative control methods.

The PID control module 150 is configured to control the actuation of the actuator 110 in proportion to a velocity difference ye between the target velocity vd calculated by the admittance modeling module 140 and the actual velocity vr measured by the encoder 120.

In addition, the PID control module 150 is configured to control the actuation of the actuator 110 by a cumulative value of the velocity difference ve.

Further, the PID control module 150 is configured to control the actuation of the actuator 110 by a difference between a previous velocity difference ve and a current velocity difference ve.

Such proportional control, integral control, and derivative control are input to the actuator 110 in a form of a single aggregate force fc.

The input energy calculating module 160, the output energy calculating module 170, and the passivity control module 180 are provided to stabilize the system by comparing, in real time, current input and output energies of the system and determining stability of the system.

The input energy calculating module 160 is configured to calculate a current input energy Ein(k) of the muscular strength enhancing robot 100.

The input energy calculating module 160 is configured to calculate the current input energy Ein(k) of the system based on the intensity of the force fh measured by the force or torque sensor 130.

The input energy calculating module 160 is configured to calculate the current input energy Ein(k) by calculating an instantaneous input energy using the force fh measured by the force or torque sensor 130 and the target velocity vd calculated by the admittance modeling module 140, and adding the calculated instantaneous input energy and a previous input energy.

The input energy calculating module 160 is configured to calculate the current input energy $E_{in}(k)$ as expressed in Equation 1.

$$E_{in}(k) = \begin{cases} E_{in}(k-1) + \Delta T(f_h(k) \cdot v_d(k)), & \text{if } f_h(k) \cdot v_d > 0 \\ E_{in}(k-1), & \text{if } f_h(k) \cdot v_d(k) \leq 0 \end{cases} \quad \text{[Equation 1]}$$

In Equation 1, "ΔT" denotes a sampling time and a constant value, and may have a sufficiently small value to enhance resolution of the system.

The output energy calculating module 170 is configured to calculate a current output energy $E_{out}(k)$ of the muscular strength enhancing robot 100. The output energy calculating module 170 is configured to calculate the current output energy $E_{out}(k)$ of the system from the force $f_c$ output from the PID control module 150.

The output energy calculating module 170 is configured to calculate the current output energy $E_{out}(k)$ by calculating an instantaneous output energy using the force $f_c$ of controlling the actuation of the actuator 110 by the PID control module 150 and the target velocity $v_d$ calculated by the admittance modeling module 140, and adding the calculated instantaneous output energy and a previous output energy.

The output energy calculating module 170 is configured to calculate the current output energy $E_{out}(k)$ as expressed in Equation 2.

$$E_{out}(k) = \begin{cases} E_{out}(k-1) + \Delta T(f_c(k) \cdot v_d(k)), & \text{if } f_c(k) \cdot v_d > 0 \\ E_{out}(k-1), & \text{if } f_c(k) \cdot v_d(k) \leq 0 \end{cases} \quad \text{[Equation 2]}$$

In Equation 1, "ΔT" denotes a sampling time and a constant value, and may have a sufficiently small value to enhance resolution of the system.

The passivity control module 180 is configured to determine the stability of the system by comparing the current input energy $E_{in}(k)$ calculated by the input energy calculating module 160 to the current output energy $E_{out}(k)$ calculated by the output energy calculating module 170.

When a value obtained by subtracting a value of the current output energy $E_{out}(k)$ from the current input energy $E_{in}(k)$ is greater than 0, the passivity control module 180 may determine that the system is passive and thus in a stable state. Conversely, the value obtained by subtracting the value of the current output energy $E_{out}(k)$ from the current input energy $E_{in}(k)$ is less than 0, the passivity control module 180 may determine that the system becomes active and unstable.

When the system is determined to be unstable, the passivity control module 180 may stabilize the system by damping the current output energy Eout(k).

The passivity control module 180 is configured to calculate a damping element β and apply the calculated damping element β to the actuator 110.

The damping element β may be calculated as expressed in Equation 3.

$$\beta(k) = \begin{cases} -\dfrac{E_{obs}(k)}{(f_c)^2 \Delta T}, & \text{if } E_{obs} < 0 \text{ and } f_c \neq 0 \\ 0, & \text{if } E_{obs} \geq 0 \text{ or } f_c = 0 \end{cases} \quad \text{[Equation 3]}$$

In Equation 3, "$E_{obs}(k)$" denotes a value obtained by subtracting a value of $E_{out}(k)$ from a value of $E_{in}(k)$ ($E_{in}(k)-E_{out}(k)$) and "$\Delta T$" denotes a sampling time.

When the value of Eobs(k) is less than 0, that is, when the current input energy Ein(k) is less than the current output energy Eout(k), the damping element β may be applied. Conversely, when the value of Eobs(k) is greater than 0, that is, when the current input energy Ein(k) is greater than the current output energy Eout(k), the damping element β may not be applied.

The actuator 110 is actuated by receiving the force fc from the PID control module 150, and configured to adjust a speed required for the actuation of the actuator 110 by receiving the damping element β from the passivity control module 180.

Figure 2:
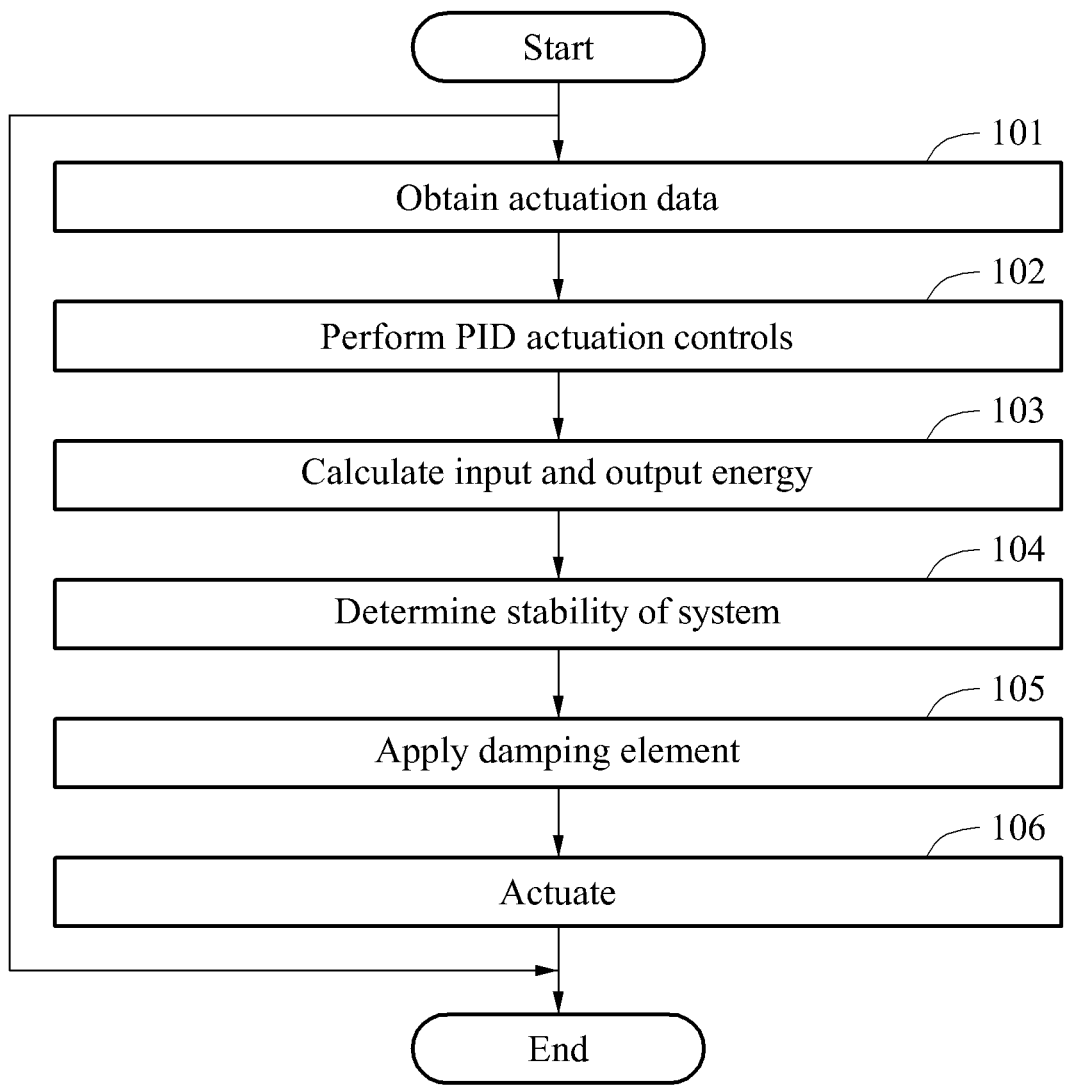
FIG. 2 is a flowchart illustrating a method of driving a muscular strength enhancing robot based on an intention of a user according to an embodiment.

FIG. 2 is a flowchart illustrating a method of driving a muscular strength enhancing robot based on an intention of a user according to an embodiment.

Referring to FIG. 2, in operation 101, actuation data is obtained. The actuation data includes a speed of the actuator 110 in a movement direction, an intensity of a force of the actuator 110, and a target velocity of the actuator 110.

In operation 102, PID controls are performed. The PID controls may be performed based on a difference between a target velocity and an actual velocity.

In operation 103, an input energy and an output energy of an entire system are calculated.

In operation 104, stability of the system is determined using the calculated input and output energy. The stability of the system may be determined through comparison of the input energy and the output energy.

In operation 105, when the system is determined to be unstable, a damping element is calculated and applied for actuation of the actuator 110.

In operation 106, the actuation of the actuator 110 is controlled through the application of the damping element. However, when the system is determined to be stable, the actuation of the actuator 110 may be controlled without applying the damping element.

Figure 3:
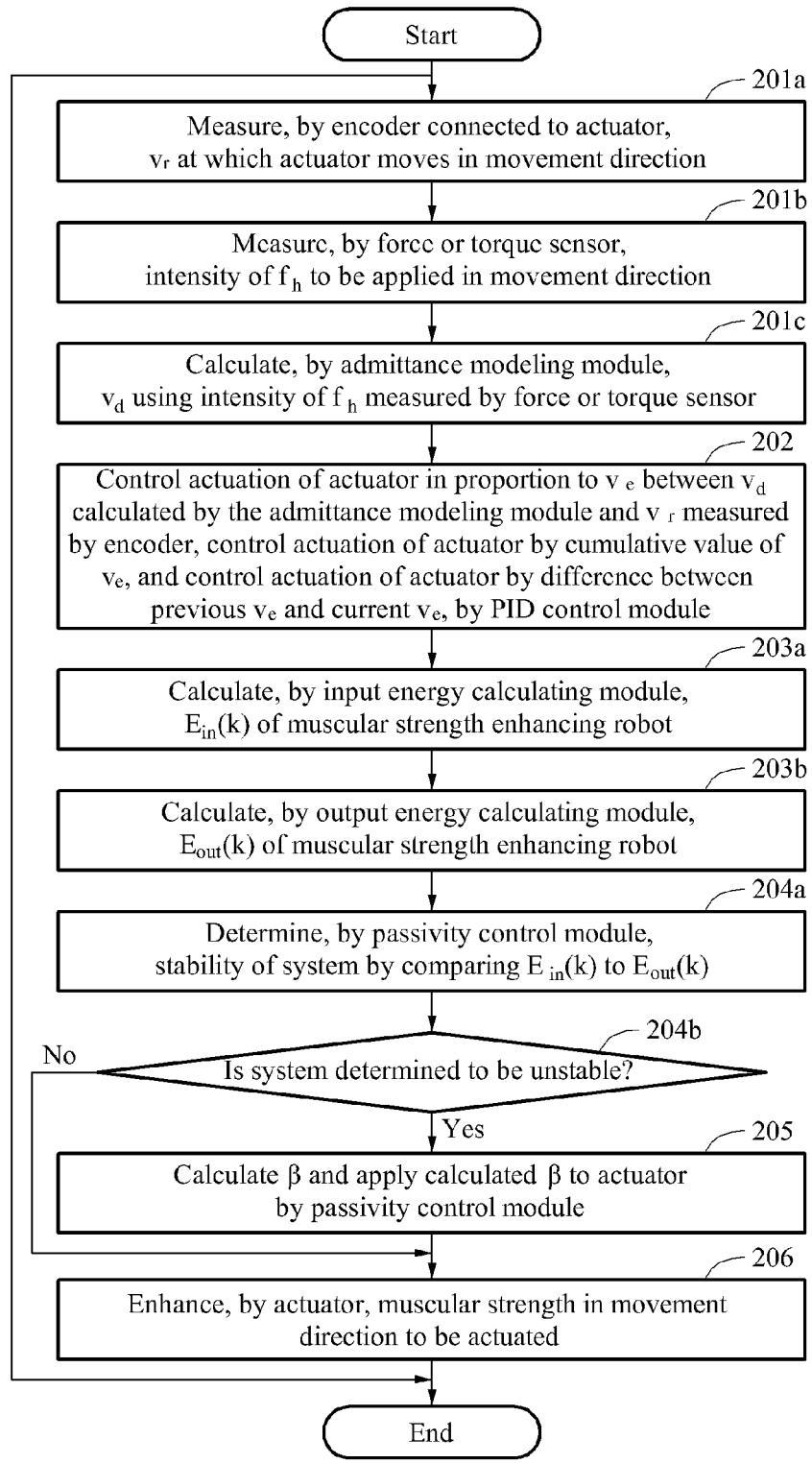
FIG. 3 is a detailed flowchart illustrating a method of driving a muscular strength enhancing robot based on an intention of a user according to an embodiment.

FIG. 3 is a detailed flowchart illustrating a method of driving a muscular strength enhancing robot based on an intention of a user according to an embodiment.

Referring to FIG. 3, in operation 201a, the encoder 120 connected to the actuator 110 measures an actual velocity vr at which the actuator 110 moves in a movement direction of a portion of a body of a user to which the actuator 110 is attached.

In operation 201b, the force or torque sensor 130 measures an intensity of a force fh to be applied in the movement direction of the portion of the body.

In operation 201c, the admittance modeling module 140 calculates a target velocity vd using the intensity of the force fh measured by the force or torque sensor 130.

In operation 202, the PDI control module 150 controls actuation of the actuator 110 in proportion to a velocity difference ye between the target velocity vd calculated by the admittance modeling module 140 and the actual velocity vr measured by the encoder 120, controls the actuation of the actuator 110 by a cumulative value of the velocity difference ve, and controls the actuation of the actuator 110 by a difference between a previous velocity difference ve and a current velocity difference ve.

In operation 203a, the input energy calculating module 160 calculates a current input energy Ein(k) of the muscular strength enhancing robot.

Here, the input energy calculating module 160 may calculate the current input energy Ein(k) by calculating an instantaneous input energy using the force fh measured by the force or torque sensor 130 and the target velocity vd calculated by the admittance modeling module 140, and adding the calculated instantaneous input energy and a previous input energy.

In detail, the current input energy $E_{in}(k)$ may be calculated as expressed in Equation 4.

$$E_{in}(k) = \begin{cases} E_{in}(k-1) + \Delta T(f_h(k) \cdot v_d(k)), & \text{if } f_h(k) \cdot v_d > 0 \\ E_{in}(k-1), & \text{if } f_h(k) \cdot v_d(k) \leq 0 \end{cases} \quad \text{[Equation 4]}$$

In Equation 4, "$\Delta T$" denotes a sampling time and a constant value.

In operation 203b, the output energy calculating module 170 calculates a current output energy $E_{out}(k)$ of the muscular strength enhancing robot.

Here, the output energy calculating module 170 may calculate the current output energy $E_{out}(k)$ by calculating an instantaneous output energy using the force $f_c$ of controlling the actuation of the actuator 110 by the PID control module 150 and the target velocity $v_d$ calculated by the admittance modeling module 140, and adding the calculated instantaneous output energy and a previous output energy.

In detail, the current output energy $E_{out}(k)$ may be calculated as expressed in Equation 5.

$$E_{out}(k) = \begin{cases} E_{out}(k-1) + \Delta T(f_c(k) \cdot v_d(k)), & \text{if } f_c(k) \cdot v_d > 0 \\ E_{out}(k-1), & \text{if } f_c(k) \cdot v_d(k) \leq 0 \end{cases} \quad \text{[Equation 5]}$$

In Equation 5, "$\Delta T$" denotes a sampling time.

In operation 204a, the passivity control module 180 determines stability of a system of the muscular strength enhancing robot by comparing the calculated current input energy $E_{in}(k)$ to the calculated current output energy $E_{out}(k)$.

When the system is determined to be unstable in operation 204b, the passivity control module 180 calculates a damping element β and applies the calculated damping element β to the actuator 110 in operation 205.

The passivity control module 180 is configured calculate the damping element β based on Equation 6.

$$\beta(k) = \begin{cases} -\dfrac{E_{obs}(k)}{(f_c)^2 \Delta T}, & \text{if } E_{obs} < 0 \text{ and } f_c \neq 0 \\ 0, & \text{if } E_{obs} \geq 0 \text{ or } f_c = 0 \end{cases} \quad \text{[Equation 6]}$$

In Equation 6, "$E_{obs}(k)$" is a value obtained by subtracting a value of $E_{out}(k)$ from a value of $E_{in}(k)$ ($E_{in}(k)-E_{out}(k)$) and "$\Delta T$" denotes a sampling time.

Here, when the value of $E_{in}(k)$ is less than the value of $E_{out}(k)$, the damping element β may be applied. When the value of $E_{in}(k)$ is greater than or equal to the value of $E_{out}(k)$, the system may be determined to be stable and the damping element β may not be applied.

In operation 206, the actuator 110 enhances a muscular strength in the movement direction of the portion of the body to be actuated.

According to embodiments described above, a muscular strength enhancing robot to be driven based on an intention of a user and a method of driving the robot are designed to output an energy through damping when a system of the robot is determined to be unstable based on a result of real-time comparison of an input energy in the system and an output energy in the system, and thus may stabilize the system by reducing an input energy which is cumulatively input and by reducing an error and a malfunction that may occur due to the instability.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A muscular strength enhancing robot to be driven based on an intention of a user, the robot comprising:
   an actuator attached to a portion of a body of the user and configured to be actuated by enhancing a muscular strength in a movement direction in which the portion moves;
   an encoder connected to the actuator and configured to measure an actual velocity $v_r$ at which the actuator moves in the movement direction;
   a force or torque sensor configured to measure an intensity of a force $f_h$ to be applied in the movement direction;
   an admittance modeling module configured to calculate a target velocity $v_d$ using the intensity of the force $f_h$ measured by the force and torque sensor;
   a proportional integral derivative (PID) control module configured to control actuation of the actuator in proportion to a velocity difference $v_e$ between the target velocity $v_d$ calculated by the admittance modeling module and the actual velocity $v_r$ measured by the encoder, control the actuation of the actuator by a cumulative value of the velocity difference $v_e$, and control the actuation of the actuator by a difference between a previous velocity difference $v_e$ and a current velocity difference $v_e$;
   an input energy calculating module configured to calculate a current input energy $E_{in}(k)$ of the robot;
   an output energy calculating module configured to calculate a current output energy $E_{out}(k)$ of the robot; and
   a passivity control module configured to determine stability of a system of the robot by comparing the calculated current input energy $E_{in}(k)$ to the calculated current output energy $E_{out}(k)$, and calculate a damping element β and apply the calculated damping element β to the actuator in response to a determination that the system is unstable.

2. The robot of claim 1, wherein the input energy calculating module is configured to calculate the current input energy $E_{in}(k)$ by calculating an instantaneous input energy using the force $f_h$ measured by the force or torque sensor and the target velocity $v_d$ calculated by the admittance modeling module, and adding the calculated instantaneous input energy and a previous input energy.

3. The robot of claim 2, wherein the current input energy $E_{in}(k)$ is calculated based on the following Equation, $$E_{in}(k) = \begin{cases} E_{in}(k-1) + \Delta T(f_h(k) \cdot v_d(k)), & \text{if } f_h(k) \cdot v_d > 0 \\ E_{in}(k-1), & \text{if } f_h(k) \cdot v_d(k) \le 0 \end{cases} \quad \text{[Equation]}$$

wherein "ΔT" denotes a sampling time.

4. The robot of claim 1, wherein the output energy calculating module is configured to calculate the current output energy $E_{out}(k)$ by calculating an instantaneous output energy using a force $f_c$ of controlling the actuation of the actuator by the PID control module and the target velocity $v_d$ calculated by the admittance modeling module, and adding the calculated instantaneous output energy and a previous output energy.

5. The robot of claim 4, wherein the current output energy $E_{out}(k)$ is calculated based on the following Equation, $$E_{out}(k) = \begin{cases} E_{out}(k-1) + \Delta T(f_c(k) \cdot v_d(k)), & \text{if } f_c(k) \cdot v_d > 0 \\ E_{out}(k-1), & \text{if } f_c(k) \cdot v_d(k) \le 0 \end{cases} \quad \text{[Equation]}$$

wherein "ΔT" denotes a sampling time.

6. The robot of claim 4, wherein the passivity control module is configured to calculate the damping element β based on the following Equation, $$\beta(k) = \begin{cases} -\dfrac{E_{obs}(k)}{(f_c)^2 \Delta T}, & \text{if } E_{obs} < 0 \text{ and } f_c \ne 0 \\ 0, & \text{if } E_{obs} \ge 0 \text{ or } f_c = 0 \end{cases} \quad \text{[Equation]}$$

wherein "$E_{obs}(k)$" is a value obtained by subtracting a value of $E_{out}(k)$ from a value of $E_{in}(k)$, $E_{in}(k)-E_{out}(k)$, and "ΔT" denotes a sampling time.

7. A method of driving a muscular strength enhancing robot based on an intention of a user, the method comprising:
   measuring, by an encoder connected to an actuator, an actual velocity $v_r$ at which the actuator moves in a movement direction in which a portion of a body of the user to which the actuator is attached moves;
   measuring, by a force or torque sensor, an intensity of a force $f_h$ to be applied in the movement direction;
   calculating, by an admittance modeling module, a target velocity $v_d$ using the intensity of the force $f_h$ measured by the force or torque sensor;
   controlling actuation of the actuator in proportion to a velocity difference $v_e$ between the target velocity $v_d$ calculated by the admittance modeling module and the actual velocity $v_r$ measured by the encoder, controlling the actuation of the actuator by a cumulative value of the velocity difference $v_e$, and controlling the actuation of the actuator by a difference between a previous velocity difference $v_e$ and a current velocity difference $v_e$, by a proportional integral derivative (PID) control module;
   calculating, by an input energy calculating module, a current input energy $E_{in}(k)$ of the robot;
   calculating, by an output energy calculating module, a current output energy $E_{out}(k)$ of the robot; and determining, by a passivity control module, stability of a system of the robot by comparing the calculated current input energy $E_{in}(k)$ to the calculated current output energy $E_{out}(k)$; and calculating a damping element β and applying the calculated damping element β to the actuator in response to a determination that the system is unstable, by the passivity control module.

8. The method of claim 7, wherein the calculating of the current input energy $E_{in}(k)$ comprises:

calculating the current input energy $E_{in}(k)$ by calculating an instantaneous input energy using the force $f_h$ measured by the force or torque sensor and the target velocity $v_d$ calculated by the admittance modeling module, and adding the calculated instantaneous input energy and a previous input energy.

9. The method of claim 7, wherein the calculating of the current output energy $E_{out}(k)$ comprises:

calculating the current output energy $E_{out}(k)$ by calculating an instantaneous output energy using a force $f_c$ of controlling the actuation of the actuator by the PID control module and the target velocity $v_d$ calculated by the admittance modeling module, and adding the calculated instantaneous output energy and a previous output energy.

10. The method of claim 8, wherein, in response to the determination that the system is unstable, the calculating of the damping element β and the applying of the calculated damping element β to the actuator by the passivity control module comprises:

calculating the damping element β based on the following Equation, $$\beta(k) = \begin{cases} -\dfrac{E_{obs}(k)}{(f_c)^2 \Delta T}, & \text{if } E_{obs} < 0 \text{ and } f_c \neq 0 \\ 0, & \text{if } E_{obs} \geq 0 \text{ or } f_c = 0 \end{cases} \quad \text{[Equation]}$$

wherein "$E_{obs}(k)$" is a value obtained by subtracting a value of $E_{out}(k)$ from a value of $E_{in}(k)$, $E_{in}(k) - E_{out}(k)$, and "$\Delta T$" denotes a sampling time.

* * * * *